United States Patent [19]
Proffitt et al.

[11] Patent Number: 5,386,718
[45] Date of Patent: Feb. 7, 1995

[54] METHOD FOR FLUID ANALYSIS

[75] Inventors: Arthur C. Proffitt; William C. Barron, both of Cody, Wyo.

[73] Assignee: Marathon Oil Company, Findlay, Ohio

[21] Appl. No.: 892,298

[22] Filed: Jun. 2, 1992

[51] Int. Cl.⁶ .................. G01N 25/20; F24D 13/02
[52] U.S. Cl. ...................... 73/61.44; 73/61.46; 392/478
[58] Field of Search ............. 73/61.46, 61.44, 61.74, 73/61.76, 861.04; 374/45, 54; 392/478

[56] References Cited

U.S. PATENT DOCUMENTS

| | | | |
|---|---|---|---|
| 2,561,249 | 7/1951 | Tomlinson | 392/478 |
| 3,304,766 | 2/1967 | Hubby | 73/61.44 |
| 4,156,127 | 5/1979 | Sako et al. | 392/478 |
| 4,813,270 | 3/1989 | Baillie | 73/61.46 |
| 4,891,969 | 1/1990 | Wayland et al. | 73/61.46 |
| 4,984,460 | 1/1991 | Isoda | 73/61.46 |

OTHER PUBLICATIONS

Geankopolis, Christie, *Transport Processes & Unit Operations*, 2nd ed., 1983, pp. 207–208, 212–213, 235.

Primary Examiner—Robert J. Warden
Assistant Examiner—L. M. Crawford
Attorney, Agent, or Firm—Jack L. Hummel; Jack E. Ebel

[57] ABSTRACT

A method determining the concentrations of fluids in a two-part fluid system. The heat loss in a test apparatus for measuring the temperatures and flow rate of a flowing fluid mixture is determined and the specific heat of the fluid mixture is calculated. Knowing the relationship between the specific heat of the fluid and its composition allows the fluid composition to be directly calculated, and hence the ratio of the two constituent fluids to be determined. A preferred heater is comprised of an electrically conductive conduit through which the fluid mixture flows which when energized efficiently heats the fluid mixture.

12 Claims, 2 Drawing Sheets

METHOD FOR FLUID ANALYSIS

FIELD OF THE INVENTION

This invention relates to the quantitative analysis of a fluid. More particularly, it relates to a method for determining the ratio of fluids in a two-component fluid system, and to a test apparatus for obtaining measurements required by the method.

BACKGROUND OF THE INVENTION

It is often important to be able to determine the ratio of fluids in a two-component fluid system. For example, in the petroleum industry, fluid produced from a hydrocarbon formation normally includes both water and oil. The water may have originated naturally in the formation or it may have been introduced into the formation as a result of secondary recovery practices. In either case, it is necessary to know the oil content of the fluid since this information is needed for determining royalty payments, productivity measurements, the cost of lifting production fluid, equipment sizing and reservoir and well management.

A number of different ways of measuring the water-/oil ratio have been suggested. Probably the most common method has been to simply introduce a sample of the fluid into a two- or three-phase test vessel where the fluids are allowed to separate from each other and from any dissolved gases, after which the individual phases are measured. This is not an entirely satisfactory method, however, because it is quite slow, requiring many hours and frequently days for the emulsions of oil, water and gas produced by wells to separate in the vessels. It may also be necessary to add expensive chemicals to enhance this separation. In addition, the apparatus is required to be semi-automatically operated, with data being acquired by visual and manual means, manually recorded and subsequently utilized in carrying out suitable mathematical calculations in order to obtain the information sought. The apparatus is necessarily large, expensive and cumbersome and is such that satisfactory operation requires great care and skill on the part of the technicians operating it. Also, use of such apparatus and its related method of testing production fluid for net oil content has frequently resulted in an error of plus or minus 10%, which is not acceptable by today's standards.

Another method is to measure the water content by measuring the electrical properties of the mixture, either by capacitance or resistance, and to obtain the oil content by subtracting the measured water content from the sample. Because the probes employed are extremely sensitive to numerous external factors, the measurements obtained in this method cannot be relied upon to yield an accurate ratio and must be frequently calibrated.

Another method is disclosed in U.S. Pat. No. 3,304,766, issued on Feb. 21, 1967, wherein the flow rate of a mixture of two liquids is measured by two different processes, one which determines the volumetric flow rate and one which determines the flow rate according to a different aspect of the mixture. The patent describes the use of a thermal instrument to determine the latter flow rate. In both cases the instrument is calibrated at 100% water, 100% oil and at various intermediate combinations of oil and water. With this information a set of curves are drawn, which are then used to interpolate the readings obtained for the fluid in question, allowing the percent of each constituent in the mixture to be estimated. Such a method does not permit rigorous calculations to be made, as only predetermined curves can be used. Further, it has inherent inaccuracies in sample definition, flow rate measurement and extrapolation. It is cumbersome and labor intensive, as calibration curves must be used for each different oil-water mix. The curves are good for only the system under investigation and must be known at the investigation temperature.

Another method is disclosed in U.S. Pat. No. 4,891,969, which issued on Jan. 9, 1990. This method is carried out by measuring the temperature increase in a fluid mixture resulting from the absorption of energy from a microwave field. The theory disclosed in the patent is based on the principle that the resulting rise in temperature of each component is proportional to its electrical thermochemical properties. In this process the level of microwave field power must be increased at smaller water fractions in order to obtain a significant temperature increase. Prior to using the test apparatus it must be calibrated with the water under investigation alone, with the oil under investigation alone and with a number of mixtures comprising intermediate oil/water ratios. Consequently, the test apparatus has problems similar to those previously mentioned. The calibration results are used to program a microprocessor to calculate the oil/water ratio from the various readings of properties taken during the testing of a fluid.

Despite the various methods proposed to determine the oil/water ratio of fluid produced from a petroleum well, no commercially demonstrated technology is available which will reliably, accurately and inexpensively determine the ratio. Further, most methods measure water content and are generally less accurate in measuring mixtures of fluids where water comprises 95% or more of the fluid, i.e., a one percent error at a 99% water cut is equal to a 100% error in the oil measurement. While this discussion has been primarily in connection with measurement problems relating to fluid produced from a hydrocarbon formation, it is noted that similar measurement problems exist in connection with other fluid systems.

It is an object of the present invention to provide a method for determining the ratio of fluids in a two-component fluid system which is accurate over the entire range of ratios from 0% to 100%, uses commonly understood thermodynamic and instrumentation technology, requires no chemicals for phase separation, lends itself to automation, is not space or capital intensive and provides accurate results. More specifically in connection with the petroleum industry, it is an object of the invention to provide such a method which is applicable to the determination of the ratio of water and oil in a system comprised of these two liquids. The ability to use such a method in the field in a remote location would be of further benefit.

BRIEF SUMMARY OF THE INVENTION

The invention utilizes an exact energy balance associated with a given mass or volumetric flow rate to calculate the specific heat of a fluid flowing through the instrument used to obtain necessary data. Knowing the relationship between the specific heat of the fluid and its composition allows the fluid composition to be directly calculated, and hence the ratio of the two constituent fluids to be determined.

In accordance with the invention, a fluid mixture is caused to flow through a conduit insulated by a layer of insulation and a measured amount of energy is added to the fluid mixture to change the temperature of the mixture. Measurements are then made of the flow rate of the fluid mixture, the temperature differential of the fluid mixture caused by the addition of energy, and the temperature differential across the layer of insulation during the addition of energy. The heat loss from the conduit to the surrounding environment can then be determined and, through application of thermodynamic principles, the specific heat of the fluid mixture can be determined. From a known relationship between the specific heat of the fluid mixture and its composition, the composition of the fluid mixture and the ratio of the two fluids making up the fluid mixture can also be determined.

The heat loss is determined by calculations involving the thermal conductivity of the insulation, the mean area of insulation and the difference between the inside and outside insulation surface temperatures, or by correlating heat loss and the temperature differential between the inner and outer surfaces of the insulation for a fluid having an accurately defined specific heat.

If a volumetric flowmeter is employed to measure the flow rate of the fluid mixture, the relationship between the concentrations of fluids in the fluid mixture and any value of specific heat of the fluid mixture is based on the product of the specific heat and the density of the fluid mixture. If a mass flowmeter is employed, the relationship is based on the value of specific heat alone.

The conduit preferably is formed of electrically conductive material which has sufficient electrical resistance to be easily and accurately measured and to function as a heater when electrical energy is directly applied, thus heating the fluid mixture flowing through it. The conduit preferably is enclosed within a sheath of insulation spaced from the conduit, and in one arrangement the conduit is comprised of a nickel/chromium/iron alloy commercially available under the name NI-CHROME.

The invention is applicable to two-component fluid systems including systems comprised of miscible or immiscible liquids, including liquids containing dissolved, suspended or dispersed solids. For the sake of clarity and simplicity, unless the context indicates otherwise, the word "fluid" will include in its meaning two liquids (either miscible or immiscible) or a liquid containing soluble, suspended or dispersed solids.

The features of the invention which enable accurate determination of the ratio of fluids in a two-component fluid system through application of thermodynamic principles are brought out in more detail in the following description, wherein the above and other aspects of the invention, as well as other benefits, will readily be apparent.

DETAILED DESCRIPTION OF THE PREFERRED EMBODIMENTS

Figure 1:
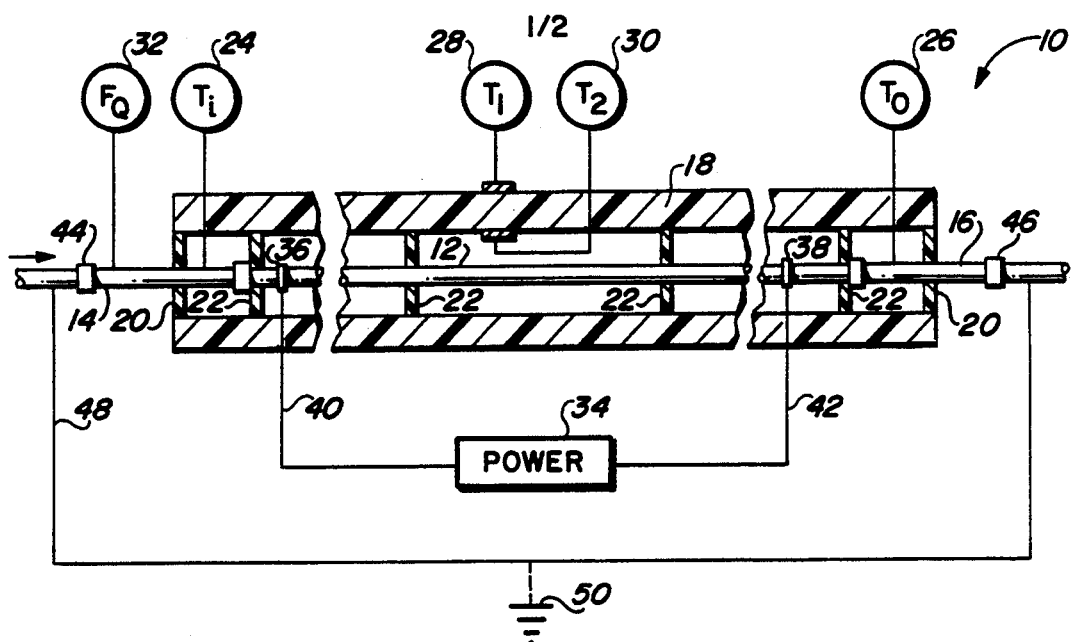
FIG. 1 is a simplified longitudinal sectional view of the apparatus used in carrying out the method of the present invention.

Referring to FIG. 1 of the drawing, the test apparatus 10 includes a conduit 12 which is connected at its upstream end to an inlet pipe 14 and at its downstream end to an outlet pipe 16. While the dimensions and configuration of the conduit 12 may vary according to the system and environment involved, in the apparatus used to generate the data presented below, it took the form of a NICHROME tube four feet in length, having an outside diameter of 0.180 inch and a wall thickness of 0.0015 inch. A tube or sheath of insulation 18 surrounds the NICHROME tube 12. The insulation employed in the test apparatus was STYROFOAM rigid foamed polystyrene plastic having a wall thickness of one inch and an inside diameter of the size used for insulating nominal 2-inch pipe. Plastic washers or discs 20 of the same material, which snugly surround the inlet and outlet conduits 14 and 16 and fit into the ends of the insulation tube 18, provide insulation at the ends of the tube. Similar discs 22 are provided to support the slender tube 12 at its ends and at points intermediate the ends.

Temperature sensors 24 and 26 are provided in the inlet and outlet pipes, respectively, at points within the insulating sleeve 18 for measuring the temperature ($T_i$) of the fluid entering the conduit 12 and the temperature ($T_o$) of the fluid exiting the conduit. The sensors may take any suitable form, such as thermocouples, thermistors and resistance thermal devices. Additional temperature sensors 28 and 30 are provided at the outer and inner wall surfaces of the insulation sleeve to measure representative outside and inside temperatures, ($T_1$ and $T_2$) respectively, of the insulation. A flowmeter 32 is shown as being connected to the inlet pipe 14 to measure fluid flow ($F_Q$) just upstream from the insulation 18. Alternatively, the flowmeter could be connected to the outlet pipe 16 to provide the same measurement.

A direct current power source 34 is connected to the conduit 12 at points 36 and 38, spaced a short distance from the inlet and outlet ends, by lines 40 and 42. The conduit 12 is electrically insulated by suitable insulating material between the pipes 14 and 16 at 44 and 46, respectively, and an electrical shunt 48 connecting the pipes 14 and 16 is electrically grounded, as indicated at 50.

The apparatus described is used to measure the energy input, the temperature increase, the flow rate of a two-component fluid, and the heat loss from the apparatus. These values are then used to determine the ratios of the fluid components through application of thermodynamic principles. Specifically, the method of the invention has its basis in the concept that the heat added to a liquid mixture causes a temperature increase dependent upon the specific heats of the liquid components. The relationship of added heat to the specific heat of a liquid is expressed by the general formula:

$$q = mc_p \Delta t + q' + q''$$

where:
  q = heat added to the apparatus, BTU/hr,
  m = mass flow rate, lbs/hr,
  $c_p$ = average specific heat (constant pressure) of the flowing substances at the average investigation temperature and pressure, BTU/lb° F., $\Delta t$ = temperature change of the mass flowing through the conduit due to heat input, q, in °F., ($T_o$-$T_i$), $q'$ = heat loss from the apparatus to the surrounding environment, BTU/hr, and $q''$ = rate of heat pick-up by the apparatus at the instant a data point is taken, BTU/hr.

The last item in the formula has to do with the transfer of heat from the surrounding atmosphere to the apparatus. This is dealt with expeditiously by recognizing that the rate of heat pick-up at the instant a data point is taken equals zero if the apparatus is at equilibrium with its environment. Therefore, by running the apparatus so that $q''=0$, the general equation becomes: $q = mc_p\Delta t + q'$.

If the insulation properties are known in sufficient detail, $q'$ can now be calculated using the following equation:

$$q' = kA_m\Delta t'$$

where:

$k$ = thermal conductivity of insulation, BTU/hr°Fft, $A_m$ = mean area of insulation for heat loss, ft$^2$, and $\Delta t'$ = temperature difference between inside and outside insulation surfaces, °F. (i.e. $T_2$-$T_1$).

While such a calculation satisfactorily determines the heat loss from the apparatus, it is preferred to run water through the apparatus and to calculate the heat loss from measurements of the flow rate, the temperature change of the water, and the temperature difference between the inside and outside insulation surfaces. Since the specific heat and density for water are known in great detail and accuracy, the heat loss, $q'$, can be calculated by means of the general equation of heat loss, modified for the condition where $q''=0$, as follows:

$$q = mc_p\Delta t + q'.$$

To utilize the measurement of flow rate, it is necessary to replace the mass flow rate, m, with its equivalent volumetric term, $F_Q\rho$, where $F_Q$ = flow rate in gallons per minute (gpm) and $\rho$ = density in pounds per gallon (lbs/gal). Converting to consistent units which requires introduction of the factor "60" to take into account that the value of the volumetric flow rate is being changed from the basis of flow per minute to flow per hour, results in the expression:

$$q = 60F_Q\rho c_p\Delta t + q'.$$

The heat added, q, can be expressed in terms of the electric power added to the system, which can be determined through the general equation:

$$P = EI = E^2/R$$

where:

P = electric power added to the system, watts/hr,

E = applied power, volts, and

R = electrical resistance of conduit heater, ohms.

Knowing that 3.413 BTU per hour equals one watt hour, the heat added may be expressed in terms of the power input to the fluid by converting BTU's to watts, whereby $q = 3.413$ P. By substituting this value for q, the equation for heat added becomes:

$$3.413P = 60F_Q\rho c_p\Delta t + q'.$$

By expressing power P, in terms of $E^2/R$ the equation becomes:

$$3.413E^2/R = 60F_Q\rho c_p\Delta t + q'$$

or $$E^2/R = P = 17.58F_Q\rho c_p\Delta t + q'/3.413.$$

With water as the fluid and under given operating conditions, every variable in this equation is known except $q'$. Thus $q'$ can be algebraically determined by means of a simple, direct calculation.

Figure 2:
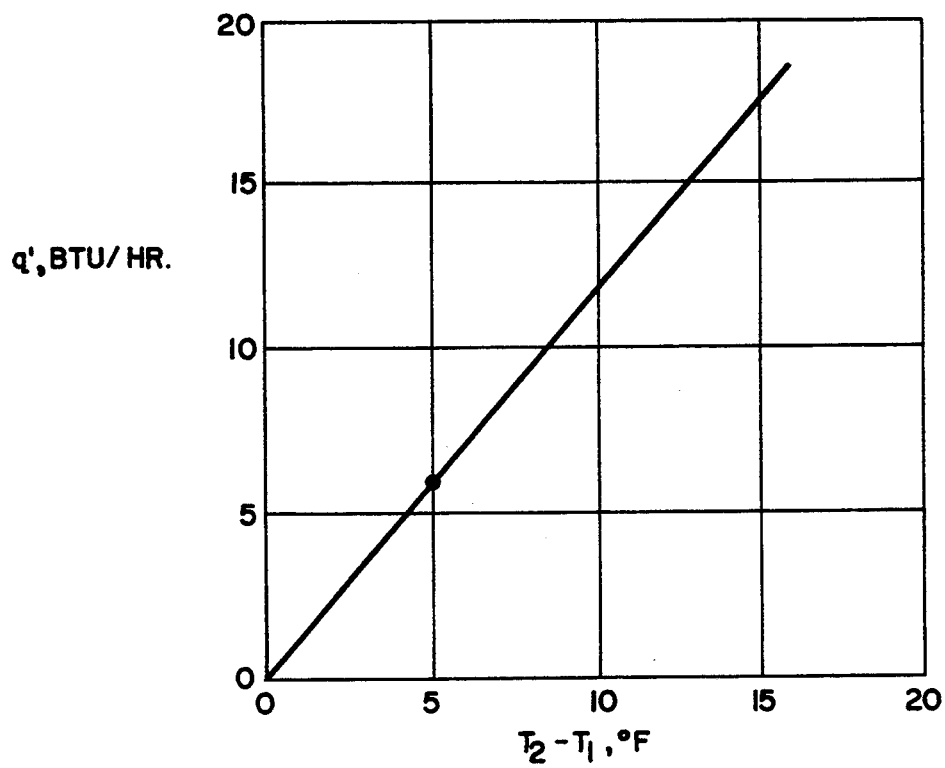
FIG. 2 is a graph showing the relationship between the temperature differential of the inner and outer surfaces of the conduit insulation and the heat loss of the system.

Going back to the equation for heat loss, $q' = kA_m\Delta t'$, and recalling that $\Delta t'$ = the temperature difference between the inside and outside insulation surfaces ($T_2$-$T_1$), it can be seen that $q'$ is linearly related to $T_2$-$T_1$ inasmuch as k and $A_m$ are constants for any given apparatus. Thus, if the values of $T_1$ and $T_2$ are noted at the time the data for calculating $q'$ is collected, the relationship between heat loss, $q'$, and $T_2$-$T_1$ can be plotted. By changing the level of power input or flow rate, new values for $q'$ and $T_2$-$T_1$ are generated. These values can be used to plot $T_2$-$T_1$ against $q'$ to produce a graph of the type shown in FIG. 2. However, it will be appreciated that the slope of the linear curve should be $kA_m$, which is a fixed number based on the design of the apparatus and which passes through the origin (0,0). Therefore, although data may be collected to provide more than one point on the graph, only a single point is required in order to draw the graph.

The relationship between $q'$ and $T_2$-$T_1$ depends on the instrument design but is independent of the fluid being evaluated. Therefore, the heat loss for any fluid run through the apparatus can be accurately determined by measuring $T_2$-$T_1$ and reading the heat loss, $q'$, from the graph. If desired, a quick and accurate check on the system operation and on all the measuring devices can be made by checking the apparatus on water prior to running the unknown fluid.

Having now defined an exact process for determining the value of heat loss $q'$ the derived equation $$P = 17.58F_Q\rho c_p\Delta t + q'/3.413$$

can be rearranged so that all the measured variables and constants for a given set of conditions are on one side as follows:

$$\rho c_p = (3.413 - q')/60F_Q\Delta t.$$

Thus, according to this equation, the product of the density and specific heat of a fluid system (A+B) can be determined without knowing any physical properties of the system except for the measurements taken for the data on the right side of the equation as a function of composition A/(A+B). Although a primary use of the method of the invention is in the petroleum industry to determine the ratio of water and oil in production fluid from a formation containing hydrocarbons, it will be appreciated that the phenomenon just stated applies to other systems as well in view of the fact that any two-component fluid system, whether comprised of two mutually soluble liquids, two immiscible liquids, or a solid and a liquid, has a single unique density and specific heat for each concentration of the two components at the investigation temperature and pressure. The method of the invention is therefore useful wherever fluids are handled, processed or used.

If a mass flowmeter is used instead of a volumetric flowmeter, the task of determining the ratio of the fluid components is simplified somewhat. This can be demonstrated by rearranging the last equation in terms of the specific heat of the fluid as follows:

$$\rho c_p = (3.413 - q')/60 F_Q \Delta t$$

Recalling that the mass flow rate, m, is equivalent to $F_Q \rho$, the latter term may be replaced by the mass flow rate as follows:

$$c_p = (3.413 - q')/60 m \Delta t$$

All that is needed to employ the method of the invention is data relating fluid specific heat to concentration of component A in the two-component fluid system A+B, and this data may be easily determined using the apparatus of the invention if not available in handbooks, textbooks, etc.

To demonstrate the invention, a fluid system comprised of water and soy bean oil was evaluated using the apparatus shown in FIG. 1. The points 36 and 38 on the tube 12 at which electrical current was applied were spaced 3 inches from the ends of the tube, making the heated conduit section 42 inches long, and the tube had an electrical resistance of 0.45 ohm. The flow of the fluid mixture was measured by a mass flowmeter at various levels of energy input at various ratios of the oil and water. Temperature measurements corresponding to $T_i$, $T_o$, $T_1$ and $T_2$ were taken and values of q, q' and q'' were measured and/or calculated as explained above. The specific heat, $c_p$, of the mixture was determined using the previously described thermodynamics procedures. The results of the test are shown in the following table.

TABLE 1

| Water % | Voltage volts | Flow Rate lbs/hr | $T_o - T_i$ °F. | $T_2 - T_1$ °F. | q BTU/ hr | q' + q'' BTU/ hr | $C_p$ BTU/ lb °F. |
|---|---|---|---|---|---|---|---|
| 100.0 | 6.600 | 13.31 | 24.10 | 8.61 | 330.38 | 10.06 | 1.000 |
| 92.2 | 6.414 | 13.39 | 23.36 | 9.16 | 312.02 | 10.71 | 0.965 |
| 89.4 | 6.130 | 13.35 | 21.27 | 10.69 | 285.00 | 12.51 | 0.950 |
| 80.4 | 5.878 | 13.28 | 21.06 | 8.63 | 262.05 | 10.10 | 0.900 |
| 69.6 | 5.807 | 13.27 | 21.80 | 8.73 | 255.76 | 10.20 | 0.850 |
| 59.7 | 5.645 | 13.17 | 22.08 | 8.12 | 241.69 | 9.50 | 0.800 |
| 50.1 | 5.458 | 13.31 | 21.68 | 8.22 | 225.94 | 9.60 | 0.750 |
| 39.2 | 5.325 | 13.27 | 22.24 | 8.77 | 215.06 | 10.26 | 0.694 |
| 30.1 | 5.105 | 13.23 | 22.03 | 9.51 | 197.66 | 11.13 | 0.640 |
| 17.0 | 4.928 | 13.15 | 22.43 | 11.09 | 184.19 | 12.98 | 0.580 |
| 7.7 | 4.770 | 13.23 | 22.66 | 11.19 | 172.57 | 13.09 | 0.534 |

Figure 3:
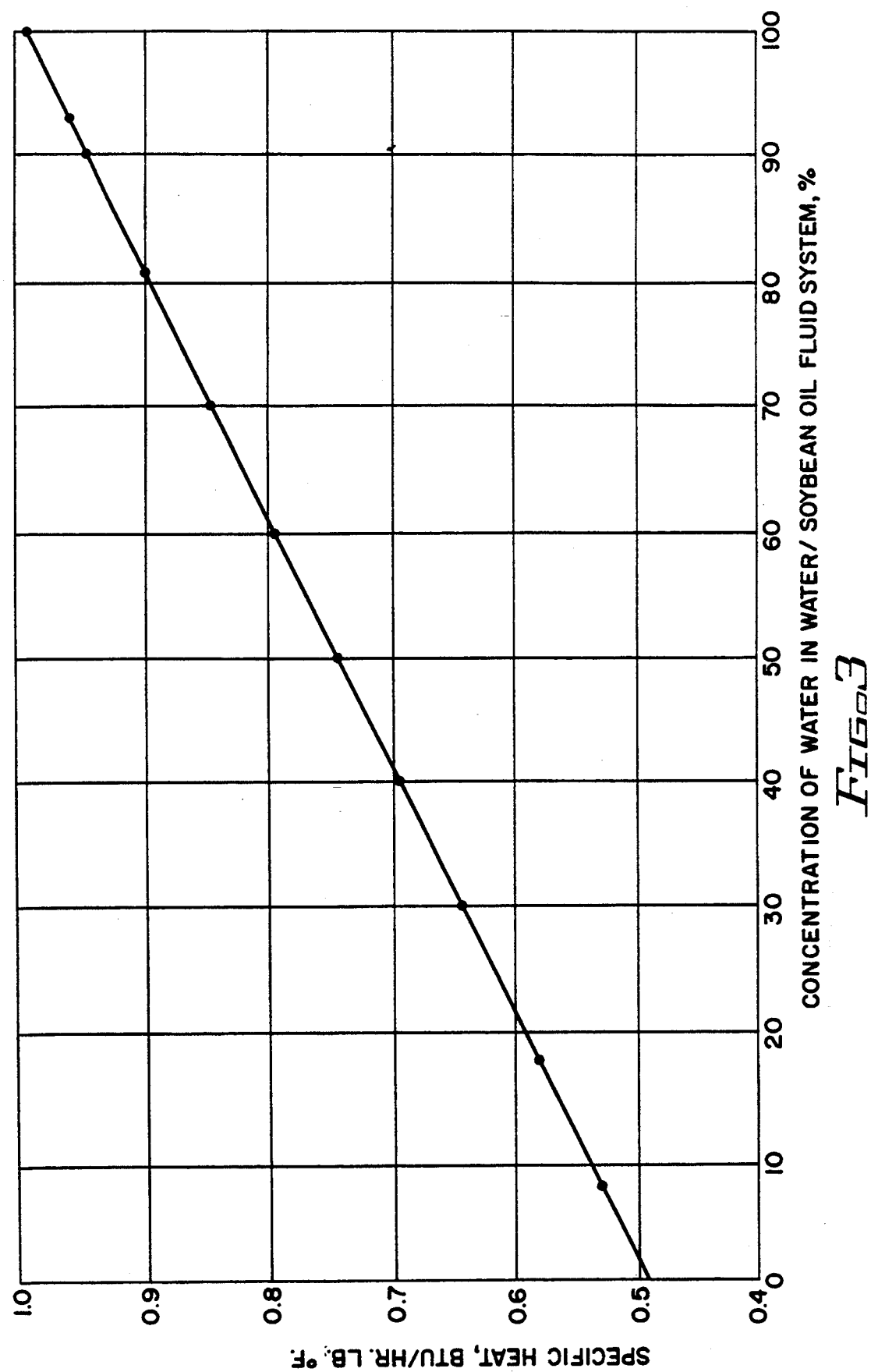
FIG. 3 is a graph showing the relationship between the percent water in an oil/water fluid system and the experimentally determined specific heat of the fluid.

The percent water in the water/soy bean oil system was plotted against the experimentally determined specific heat of the system as shown in FIG. 3. As can be seen, the resulting curve is a straight line beginning at a point on the ordinate corresponding to 100% water in the system at the specific heat of water and ending at a point on the ordinate corresponding to 100% oil in the system at the experimentally determined specific heat of oil. The graph completely confirms the method of the invention, since the relationship between the composite specific heat of two immiscible liquids is a straight line.

As mentioned previously, it may be necessary to develop specific heat data at the desired conditions through use of the apparatus of the invention, inasmuch as data for specific mutually soluble, miscible fluids or solutions may not be available from existing literature at the desired investigation temperatures and pressures. This is a simple matter since the apparatus measures true bulk properties. Enough data should be taken in such a case to enable a smooth curve to be drawn through the points for the concentrations in the area of interest.

It can be appreciated that the relationship between the specific heat and the concentration of a component in a two-component fluid system whose flow is measured by a mass flowmeter, as well as the relationship between the product of specific heat and density and the concentration of a component in a two-component fluid system whose flow is measured by a volumetric flowmeter, must vary enough to permit the measurements to discriminate different concentration values. Although such a situation seldom occurs, it is a constraint that should be considered prior to use of the apparatus.

As noted, the conduit employed in the apparatus used to generate the data discussed above was formed from NICHROME alloy. While the invention is not limited to use of such material, there are nonetheless certain parameters that the material should meet. The material from which the conduit is formed, whether it is a metal alloy or a nonmetal such as carbon, needs to be resistant to corrosion from the fluids being evaluated. Further, the temperature coefficient of resistivity for the material needs to be very low so that the electrical resistance of the conduit is essentially constant over the expected operating temperature range.

In addition, the electrical resistance of the conduit needs to be high enough to be easily and accurately measured, as does the operating voltage. For example, a copper tube having the same dimensions as the NICHROME tube previously described would have an electrical resistance of about 0.0077 ohm, and thus require only 0.77 applied volts to put out 100 watts, as compared to 0.45 ohm and 6.71 applied volts for the NICHROME conduit. The 0.0077 ohm resistance, in particular, is very difficult to measure accurately. Since the electrical resistance of the conduit is a function of the length and cross-sectional area of the conduit and the electrical resistivity of the material from which the conduit is formed, a desired value of electrical resistance can be designed into the conduit. For the purpose of easily and accurately measuring the electrical resistance of the conduit and the operating voltage, the electrical resistance should be at least 0.3 ohm and the operating voltage in the range of 5-24 volts.

On the other hand, it is not desirable to utilize a conduit formed from a material having very high electrical resistance since such a conduit could force enough power through a conductive fluid to give significant, but hard to measure, power and hence produce erroneous results. For the particular condition where one is looking at very high water contents, such as, for example, 99%, the electrical resistance of the conduit should be no more than about 0.0005 times the electrical resistance of the fluid. The apparatus of the invention described previously, for example, has an electrical resistance of about 0.0002 times that of a 28% sodium chloride brine. Thus the apparatus meets this criteria even for a highly conductive brine.

If it is not desirable for the conduit to be in contact with the fluid being examined, the conduit could be coated or lined with electrically insulating material. Further, it is not necessary that direct current be used to power the apparatus. Alternating current will work as well.

If desired, the heater may take the form of a conduit covered with an electrical insulator, which is then wrapped with a high resistivity wire or ribbon, which in turn is then covered with another electrically insulating material. Some commercially available heaters which operate in a similar fashion are comprised of electrically conductive and resistive foil material laminated between two thin sheets of electrical insulation. While these heater designs function adequately, it is nevertheless preferred to use a conduit such as the one described in connection with FIG. 1 which has an easily and accurately measurable resistance so that it can serve as the electrical heater.

There are several reasons why this is preferred. Since the entire conduit between the electric terminals is available for heat transfer, the area of the conduit so available is the largest theoretically possible and is used anytime current is applied. Further, there is no more efficient way to add heat to the flowing fluid due to the fact that the overall heat transfer coefficient will be higher when the conduit is used as the heater because there are fewer heat transfer barriers in such an arrangement. Due to these features, the combination conduit-heater will have a lower temperature for a given area and will therefore not be as susceptible to failure from burn-out or hot spots. It will also have less heat loss so that the same percent error in the heat loss measurement will be a smaller absolute number and produce less error in the measurement. In addition, the dual use of the conduit allows the apparatus to be used in higher temperature applications and minimizes the size and mass of the conduit in view of the fact that no temperature sensitive electrical insulating materials are required between the heater and the conduit. Response is also improved as the mass of the instrument is minimized.

The apparatus of the invention is comprised of readily available components and the necessary measurements can be made by standard measuring instruments. The invention may be used wherever the ratio of one fluid component in a two-component fluid system is desired to be determined, one practical application out of many being to measure the oil/water ratio in fluid produced from a hydrocarbon formation. In such an application, and in others, the invention readily lends itself to use in the field, since the size of the apparatus is small and the required energy input can be from a small generator or battery.

The invention makes use of an exact energy balance associated with a given mass or volumetric flow rate to calculate the specific heat of a fluid flowing through the investigative instrument described above, which requires the accurate measurement of flow rate, energy changes and temperatures. The instrument could therefore be used wherever such measurements are significant, such as in measuring heat losses or gains due to chemical reactions, polymerizations or phase changes. The instrument thus has utility wherever such measurements are useful in addition to its described use in determining the ratios of components in a two-component fluid system.

It will be apparent that the invention need not necessarily be limited to all the specific details described in connection with the preferred embodiment, except as such details may be required by the appended claims, and that changes to certain features of the preferred embodiment which do not alter the overall basic function and concept of the invention are contemplated.

What is claimed is:

1. A method of determining the ratio of fluids in a fluid mixture consisting of two different fluids, comprising the steps of:
    providing a fluid mixture comprised of two different fluids;
    flowing the fluid mixture through a conduit insulated by a layer of insulation;
    adding a measured amount of energy to the flowing fluid mixture to heat the same;
    measuring the volumetric or mass flow rate of the fluid mixture directly with a flowmeter during the addition of energy to the fluid mixture;
    determining the temperature differential of the fluid mixture within the conduit insulated by said layer of insulation which is caused by the addition of energy thereto;
    measuring the temperature differential across the layer of insulation during said addition of energy;
    determining the heat loss from the conduit to the surrounding environment from a known relationship between said heat loss and said measured temperature difference across the layer of insulation;
    determining the specific heat of the fluid mixture from the thermodynamic relationship that the added heat is equal to the product of the flow rate and temperature differential of the fluid mixture minus the heat loss; and
    determining from a known relationship between the specific heat of the fluid mixture and the composition thereof the composition of the fluid mixture and the ratio of the two fluids, the known relationship being obtained from published data or from a plot of the concentration of one of the components in the fluid mixture against the specific heat of the fluid mixture.

2. The method of claim 1, wherein the heat loss is determined by correlating heat loss and temperature differential across the layer of insulation using a fluid having a known specific heat at the investigation temperature.

3. The method of claim 1, wherein the conduit is comprised of electrically conductive material having a sufficiently high resistance so as to act as a heater when electrical energy is applied thereto, and wherein the measured amount of energy added to the fluid mixture comprises electrical energy applied directly to the conduit.

4. The method of claim 3, wherein the electrically conductive material of the conduit has an electrical resistance of at least 0.3 ohm.

5. The method of claim 4, wherein the electrically conductive material of the conduit has an electrical resistance which is not greater than about 0.0005 times the electrical resistance of the fluid mixture.

6. The method of claim 4, wherein the electrical energy applied to the conduit is in the range of about 5-24 volts.

7. The method of claim 3, wherein the conduit is comprised of an alloy of nickel, chromium and iron.

8. The method of claim 1, wherein the flow rate of the fluid mixture is measured by means of a mass flowmeter.

9. The method of claim 1, wherein the flow rate of the fluid mixture is measured by means of a volumetric flowmeter.

10. The method of claim 1, wherein the fluid mixture is comprised of two immiscible liquids.

11. The method of claim 10, wherein the two immiscible liquids comprise oil and water.

12. The method of claim 1, wherein the method is conducted under conditions such that the rate of heat pickup up from the surrounding environment at the instant a data point is taken equals zero.

* * * * *